United States Patent
Hanina et al.

(10) Patent No.: US 11,004,554 B2
(45) Date of Patent: *May 11, 2021

(54) METHOD AND APPARATUS FOR IDENTIFICATION

(71) Applicant: AIC Innovations Group, Inc., New York, NY (US)

(72) Inventors: Adam Hanina, New York, NY (US); Lei Guan, Jersey City, NJ (US)

(73) Assignee: AIC Innovations Group, Inc., Mount Kisco, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/737,478

(22) Filed: Jan. 8, 2020

(65) Prior Publication Data

US 2020/0143144 A1 May 7, 2020

Related U.S. Application Data

(63) Continuation of application No. 16/188,837, filed on Nov. 13, 2018, now Pat. No. 10,565,431, which is a
(Continued)

(51) Int. Cl.
*G06K 9/00* (2006.01)
*G16H 20/10* (2018.01)
(Continued)

(52) U.S. Cl.
CPC ......... *G16H 20/10* (2018.01); *G06K 9/00221* (2013.01); *G06K 9/00335* (2013.01);
(Continued)

(58) Field of Classification Search
CPC .......... G06K 9/00221; G06K 9/00335; G06K 9/00711; G16H 10/60; G06N 20/00
See application file for complete search history.

(56) References Cited

U.S. PATENT DOCUMENTS

| 3,814,845 A | 6/1974 | Hurlbrink et al. |
| 5,065,447 A | 11/1991 | Barnsley et al. |
| (Continued) | | |

OTHER PUBLICATIONS

Ammouri et al., *Face and Hands Detection and Tracking Applied to the Monitoring of Medication Intake*, Computer and Robot Vision, 2008. CRV '08. Canadian Conference on, vol. No., pp. 147, 154, May 28-30, 2008.
(Continued)

*Primary Examiner* — Jonathan R Messmore
(74) *Attorney, Agent, or Firm* — Fish & Richardson P.C.

(57) ABSTRACT

A method and system for de-identifying a video sequence are provided. The method may include the steps of capturing a video sequence, comprising a number of individual frames, including one or more users performing one or more actions, and using activity recognition to recognize one of the one or more actions. One or more of the plurality of frames may be defined as comprising the recognized one or more actions, and a portion of the one or more of the plurality of frames may be identified to remain visible. The non-identified portions of the one or more of the plurality of frames and the non-defined frames may be de-identified. This method may be applied to the determination of whether a user has ingested a medication pill.

20 Claims, 6 Drawing Sheets

Related U.S. Application Data continuation of application No. 15/595,441, filed on May 15, 2017, now Pat. No. 10,133,914, which is a continuation of application No. 14/990,389, filed on Jan. 7, 2016, now Pat. No. 9,652,665, which is a continuation of application No. 13/674,209, filed on Nov. 12, 2012, now Pat. No. 9,256,776.

(60) Provisional application No. 61/582,969, filed on Jan. 4, 2012.

(51) Int. Cl.
  *G06N 20/00* (2019.01)
  *G16H 10/60* (2018.01)
  *G16H 30/40* (2018.01)

(52) U.S. Cl.
  CPC ......... *G06K 9/00711* (2013.01); *G06N 20/00* (2019.01); *G16H 10/60* (2018.01); *G16H 30/40* (2018.01)

(56) References Cited

U.S. PATENT DOCUMENTS

| | | | |
|---|---|---|---|
| 5,441,047 A | 8/1995 | David et al. |
| 5,544,649 A | 8/1996 | David et al. |
| 5,596,994 A | 1/1997 | Bro |
| 5,619,991 A | 4/1997 | Sloane |
| 5,646,912 A | 7/1997 | Cousin |
| 5,752,621 A | 5/1998 | Passamante |
| 5,764,296 A | 6/1998 | Shin |
| 5,810,747 A | 9/1998 | Brundy et al. |
| 5,911,132 A | 6/1999 | Sloane |
| 5,961,446 A | 10/1999 | Beller et al. |
| 5,963,136 A | 10/1999 | Obrien |
| 6,151,521 A | 11/2000 | Guo et al. |
| 6,233,428 B1 | 5/2001 | Fryer |
| 6,234,343 B1 | 5/2001 | Papp |
| 6,283,761 B1 | 9/2001 | Joao |
| 6,380,858 B1 | 4/2002 | Yarin et al. |
| 6,409,661 B1 | 6/2002 | Murphy |
| 6,421,650 B1 | 7/2002 | Goetz et al. |
| 6,483,993 B1 | 11/2002 | Misumi et al. |
| 6,484,144 B2 | 11/2002 | Martin et al. |
| 6,535,637 B1 | 3/2003 | Wootton et al. |
| 6,611,206 B2 | 8/2003 | Eshelman et al. |
| 6,628,835 B1 | 9/2003 | Brill et al. |
| 6,705,991 B2 | 3/2004 | Bardy |
| 6,879,970 B2 | 4/2005 | Shiffman et al. |
| 6,988,075 B1 | 1/2006 | Hacker |
| 7,184,047 B1 | 2/2007 | Crampton |
| 7,184,075 B2 | 2/2007 | Reiffel |
| 7,256,708 B2 | 8/2007 | Rosenfeld et al. |
| 7,277,752 B2 | 10/2007 | Matos |
| 7,304,228 B2 | 12/2007 | Bryden et al. |
| 7,307,543 B2 | 12/2007 | Rosenfeld et al. |
| 7,317,967 B2 | 1/2008 | DiGianfilippo et al. |
| 7,340,077 B2 | 3/2008 | Gokturk |
| 7,395,214 B2 | 7/2008 | Shillingburg |
| 7,415,447 B2 | 8/2008 | Shiffman et al. |
| 7,448,544 B1 | 11/2008 | Louie et al. |
| 7,562,121 B2 | 7/2009 | Berisford et al. |
| 7,627,142 B2 | 12/2009 | Kurzweil et al. |
| 7,657,443 B2 | 2/2010 | Crass et al. |
| 7,692,625 B2 | 4/2010 | Morrison et al. |
| 7,712,288 B2 | 5/2010 | Ramasubramanian et al. |
| 7,747,454 B2 | 6/2010 | Bartfeld et al. |
| 7,761,311 B2 | 7/2010 | Clements et al. |
| 7,769,465 B2 | 8/2010 | Matos |
| 7,774,075 B2 | 8/2010 | Lin et al. |
| 7,874,984 B2 | 1/2011 | Elsayed et al. |
| 7,881,537 B2 | 2/2011 | Ma et al. |
| 7,908,155 B2 | 3/2011 | Fuerst et al. |
| 7,912,733 B2 | 3/2011 | Clements et al. |
| 7,945,450 B2 | 5/2011 | Strawder |
| 7,956,727 B2 | 6/2011 | Loncar |
| 7,983,933 B2 | 7/2011 | Karkanias et al. |
| 8,065,180 B2 | 11/2011 | Hufford et al. |
| 8,321,284 B2 | 11/2012 | Clemets et al. |
| 8,370,262 B2 | 2/2013 | Blessing |
| 8,606,595 B2 | 12/2013 | Udani |
| 9,256,776 B2 | 2/2016 | Hanina et al. |
| 9,652,665 B2 | 5/2017 | Hanina et al. |
| 2001/0049673 A1 | 12/2001 | Dulong et al. |
| 2001/0056358 A1 | 12/2001 | Dulong et al. |
| 2002/0026330 A1 | 2/2002 | Klein |
| 2002/0093429 A1 | 7/2002 | Matsushita et al. |
| 2002/0143563 A1 | 10/2002 | Hufford et al. |
| 2003/0036683 A1 | 2/2003 | Kehr et al. |
| 2003/0058341 A1 | 3/2003 | Brodsky et al. |
| 2003/0164172 A1 | 9/2003 | Chumas et al. |
| 2003/0190076 A1 | 10/2003 | Delean |
| 2003/0225325 A1 | 12/2003 | Kagermeier et al. |
| 2004/0100572 A1 | 5/2004 | Kim |
| 2004/0107116 A1 | 6/2004 | Brown |
| 2004/0155780 A1 | 8/2004 | Rapchak |
| 2005/0144150 A1 | 6/2005 | Ramamurthy et al. |
| 2005/0149361 A1 | 7/2005 | Saus et al. |
| 2005/0180610 A1 | 8/2005 | Kato et al. |
| 2005/0182664 A1 | 8/2005 | Abraham-Fuchs et al. |
| 2005/0234381 A1 | 10/2005 | Niemetz et al. |
| 2005/0267356 A1 | 12/2005 | Ramasubramanian et al. |
| 2006/0066584 A1 | 3/2006 | Barkan |
| 2006/0218011 A1 | 9/2006 | Walker et al. |
| 2006/0238549 A1 | 10/2006 | Marks |
| 2006/0294108 A1 | 12/2006 | Adelson et al. |
| 2007/0008112 A1 | 1/2007 | Covannon et al. |
| 2007/0008113 A1 | 1/2007 | Spoonhower et al. |
| 2007/0030363 A1 | 2/2007 | Cheatle et al. |
| 2007/0118389 A1 | 5/2007 | Shipon |
| 2007/0194034 A1 | 8/2007 | Vasiadis |
| 2007/0233035 A1 | 10/2007 | Wehba et al. |
| 2007/0233049 A1 | 10/2007 | Wehba et al. |
| 2007/0233050 A1 | 10/2007 | Wehba et al. |
| 2007/0233281 A1 | 10/2007 | Wehba et al. |
| 2007/0233520 A1 | 10/2007 | Wehba et al. |
| 2007/0233521 A1 | 10/2007 | Wehba et al. |
| 2007/0273504 A1 | 11/2007 | Tran |
| 2007/0288266 A1 | 12/2007 | Sysko et al. |
| 2008/0000979 A1 | 1/2008 | Poisner |
| 2008/0093447 A1 | 4/2008 | Johnson et al. |
| 2008/0114226 A1 | 5/2008 | Music et al. |
| 2008/0114490 A1 | 5/2008 | Jean-Pierre |
| 2008/0119958 A1 | 5/2008 | Bear et al. |
| 2008/0138604 A1 | 6/2008 | Kenney et al. |
| 2008/0140444 A1 | 6/2008 | Karkanias et al. |
| 2008/0162192 A1 | 7/2008 | Vonk et al. |
| 2008/0172253 A1 | 7/2008 | Chung et al. |
| 2008/0178126 A1 | 7/2008 | Beeck et al. |
| 2008/0201174 A1 | 8/2008 | Ramasubramanian et al. |
| 2008/0219493 A1 | 9/2008 | Tadmor |
| 2008/0275738 A1 | 11/2008 | Shillingburg |
| 2008/0290168 A1 | 11/2008 | Sullivan et al. |
| 2008/0294012 A1* | 11/2008 | Kurtz ................ A61B 5/445 600/300 |
| 2008/0297589 A1 | 12/2008 | Kurtz et al. |
| 2008/0298571 A1* | 12/2008 | Kurtz ................ H04N 7/142 379/156 |
| 2008/0303638 A1 | 12/2008 | Nguyen et al. |
| 2009/0012818 A1 | 1/2009 | Rodgers |
| 2009/0018867 A1 | 1/2009 | Reiner |
| 2009/0043610 A1 | 2/2009 | Nadas et al. |
| 2009/0048871 A1 | 2/2009 | Skomra |
| 2009/0095837 A1 | 4/2009 | Lindgren |
| 2009/0128330 A1 | 5/2009 | Monroe |
| 2009/0159714 A1 | 6/2009 | Coyne, III et al. |
| 2009/0217194 A1 | 8/2009 | Martin et al. |
| 2009/0245655 A1 | 10/2009 | Matsuzaka |
| 2010/0042430 A1 | 2/2010 | Bartfield |
| 2010/0050134 A1 | 2/2010 | Clarkson |
| 2010/0057646 A1 | 3/2010 | Martin et al. |
| 2010/0092093 A1 | 4/2010 | Akatsuka et al. |
| 2010/0136509 A1 | 6/2010 | Mejer et al. |
| 2010/0138154 A1 | 6/2010 | Kon |

(56) References Cited

U.S. PATENT DOCUMENTS

| | | |
|---|---|---|
| 2010/0255598 A1 | 10/2010 | Melker |
| 2010/0262436 A1 | 10/2010 | Chen et al. |
| 2010/0316979 A1 | 12/2010 | Von Bismarck |
| 2011/0021952 A1 | 1/2011 | Vallone |
| 2011/0119073 A1 | 5/2011 | Hanina et al. |
| 2011/0153360 A1 | 6/2011 | Haninia et al. |
| 2011/0161109 A1 | 6/2011 | Pinsonneault et al. |
| 2011/0161999 A1* | 6/2011 | Klappert ............ H04N 21/4755 725/25 |
| 2011/0195520 A1 | 8/2011 | Leider et al. |
| 2011/0275051 A1 | 11/2011 | Hanina et al. |
| 2012/0011575 A1 | 1/2012 | Cheswick et al. |
| 2012/0075464 A1 | 3/2012 | Derenne et al. |
| 2012/0081551 A1 | 4/2012 | Mizuno et al. |
| 2012/0140068 A1 | 6/2012 | Monroe et al. |
| 2012/0182380 A1 | 7/2012 | Ohmae et al. |

OTHER PUBLICATIONS

Batz, et al. *A computer Vision System for Monitoring Medication Intake*, in Proc. IEEE 2nd Canadian Conf. on Computer and Robot Vision, Victoria, BC, Canada, 2005, pp. 362-369.

Bilodeau et al. *Monitoring of Medication Intake Using a Camera System*, Journal of Medical Systems 2011. [retrieved on Feb. 18, 2013] Retrieved from ProQuest Technology Collection.

Chen, Pauline W., *Texting as a Health Tool for Teenagers*, The New York Times, Nov. 5, 2009, http://www.nytimes.com/2009/11/05/health/05chen.html?_r=1&emc=.

Danya International, Inc., *Pilot Study Using Cell Phones for Mobile Direct Observation Treatment to Monitor Medication Compliance of TB Patients*, Mar. 20, 2009, www.danya.com/MDOT.asp.

Final Office Action from PTO, Cited in AI-0001-U1 (U.S. Appl. No. 12/620,686), (dated May 8, 2012), 1-24.

Final Office Action from PTO, Cited in AI-0001-U2 (U.S. Appl. No. 13/558,377), dated May 7, 2013, 1-29.

Final Office Action from PTO, Cited in AI-0002-U1 (U.S. Appl. No. 12/646,383), (dated May 8, 2012), 1-31.

Final Office Action from PTO, Cited in AI-0002-U2 (U.S. Appl. No. 13/588,380), (dated Mar. 1, 2013), 1-27.

Final Office Action from PTO, Cited in AI-0003-U1 (U.S. Appl. No. 12/646,603), (dated Feb. 1, 2012), 1-17.

Final Office Action from PTO, Cited in AI-0004-U1 (U.S. Appl. No. 12/728,721), (dated Apr. 12, 2012), 1-31.

Final Office Action from PTO, Cited in AI-0005-U1 (U.S. Appl. No. 12/815,037), (dated Sep. 13, 2012), 1-15.

Final Office Action from PTO, Cited in AI-0006-U1 (U.S. Appl. No. 12/899,510), (dated Aug. 28, 2013).

Final Office Action from PTO, Cited in AI-0008-U1 (U.S. Appl. No. 12/898,338), dated Nov. 9, 2012), 1-12.

Final Office Action from PTO, Cited in AI-0012-U1 (U.S. Appl. No. 13/189,518), (dated Jul. 23, 2013), 1-16.

Fook et al. *Smart Mote-Based Medical System for Monitoring and Handling Medication Among Persons with Dementia*. ICOST 2007, LNCS 4541, pp. 54-62, 2007.

*Global Tuberculosis Control: A short update to the 2009 report*, World Health Organization, (2009).

Huynh et al., *Real time detection, tracking and recognition of medication intake*. World Academy of Science, Engineering and Technology 60 (2009), 280-287.

International Preliminary Report on Patentability, cited in AI-0001-PCT1 (PCT/US2010/056935) (dated May 31, 2012), 1-8.

International Preliminary Report on Patentability, cited in AI-0020-PCT1 (PCT/US2013/020026) dated May 5, 2015 (13 pages).

Mintchell, *Exploring the Limits of Machine Vision*, Automating World, Oct. 1, 2011.

Non-Final Office Action from PTO, Cited in AI-0001-111 (U.S. Appl. No. 12/620,686), (dated Dec. 21, 2011), 1-78.

Non-Final Office Action from PTO, Cited in AI-0001-U2 (U.S. Appl. No. 13/558,377), (dated Oct. 22, 2012), 1-21.

Non-Final Office Action from PTO, Cited in AI-0002-111 (U.S. Appl. No. 12/646,383), (dated Dec. 22, 2011),1-78.

Non-Final Office Action from PTO, Cited in AI-0002-U2 (U.S. Appl. No. 13/558,380), (dated Oct. 4, 2012), 1-20.

Non-Final Office Action from PTO, Cited in AI-0003-U1 (U.S. Appl. No. 12/646,603), (dated Oct. 13, 2011),1-74.

Non-Final Office Action from PTO, Cited in AI-0003-U1 (U.S. Appl. No. 12/646,603), (dated Jun. 13, 2013), 1-16.

Non-Final Office Action from PTO, Cited in AI-0004-U1 (U.S. Appl. No. 12/728,721), (dated Jan. 6, 2012), 1-31.

Non-Final Office Action from PTO, Cited in AI-0004-U1 (U.S. Appl. No. 12/728,721), (dated May 9, 2013), 1-25.

Non-Final Office Action from PTO, Cited in AI-0005-U1 (U.S. Appl. No. 12/815,037), (dated Mar. 28, 2012),1-17.

Non-Final Office Action from PTO, Cited in AI-0005-U1 (U.S. Appl. No. 12/815,037), (dated Jul. 18, 2013), 1-19.

Non-Final Office Action from PTO, Cited in AI-0006-U1 (U.S. Appl. No. 12/899,510), (dated Jan. 23, 2013), 1-20.

Non-Final Office Action from PTO, Cited in AI-0008-U1 (U.S. Appl. No. 12/898,338), (dated Jun. 19, 2012), 1-16.

Non-Final Office Action from PTO, Cited in AI-0012-U1 (U.S. Appl. No. 13/189,518), (dated Dec. 21, 2012), 1-10.

Non-Final Office Action from PTO, Cited in AI-0013-U1 (U.S. Appl. No. 13/235,387), dated Sep. 12, 2013), 1-16.

Osterberg, Lars and Blaschke, Terrence, *Adherence to Medication*, New England Journal of Medicine 2005; 353:487-97, Aug. 4, 2005.

PCT Search report and written opinion, Cited in AI-0001-PCT1 (PCT/US2010/56935, (dated Jan. 12, 2011), 1-9.

PCT Search report and written opinion, Cited in AI-0005-PCT1 (PCT/US2011/35093, (dated Sep. 12, 2011), 1-8.

PCT Search report and written opinion, Cited in AI-0006-PCT1 (PCT/US11/54666), (dated Feb. 28, 2012), 1-13.

PCT Search report and written opinion, Cited in AI-0008-PCT1 (PCT/US11/54668), dated Feb. 28, 2012, 1-12.

PCT Search report and written opinion, Cited in AI-0012-PCT1 (PCT/US12/41785), (dated Aug. 17, 2012), 1-10.

PCT Search report and written opinion, Cited in AI-0013-PCT1 (PCT/US12/42843), (dated Aug. 31, 2012), 1-8.

PCT Search report and written opinion, Cited in AI-0018-PCT1 (PCT/US2012/051554), (dated Oct. 19, 2012), 1-12.

PCT Search report and written opinion, Cited in AI-0019-PCT (PCT/US12/59139), (dated Dec. 18, 2012), 1-15.

PCT Search report and written Opinion, Cited in AI-0020-PCT1 (PCT/US13/20026), (dated Aug. 5, 2013), 1-14.

PR Newswire. *Pilot Study Using Video Cell Phones for Mobile Direct Observation (MOOT) to Monitor Medication Compliance of TB Patients*, New York: Mar 23, 2009.

*Super-Resolution*, Wikipedia, (Oct. 5, 2010).

University of Texas, GuideView, Mar. 15, 2007, http://www.sahs.uth.tmc.edu/MSriram/GuideView/.

Valin, et al. *Video Surveillance of Medication intake*, Int. Conf. of the IEEE Engineering in Medicine and Biology Society, New York City, USA, Aug. 2006.

Wang et al. *Recent Developments in human motion analysis*. Pattern Recognition 36 (220) 585-601 (Nov. 2001).

Whitecup, Morris S., *2008 Patient Adherence Update: New Approaches for Success*, www.guideline.com, The Trend Report Series, (Oct. 1, 2008).

\* cited by examiner

METHOD AND APPARATUS FOR IDENTIFICATION

CROSS REFERENCE TO RELATED APPLICATIONS

This application is a continuation of U.S. patent application Ser. No. 16/188,837, filed Nov. 13, 2018, to Hanina et al., titled "Method and Apparatus for Identification", which is a continuation of U.S. patent application Ser. No. 15/595,441, filed May 15, 2017 to Hanina et al., titled "Identification and De-Identification Within A Video Sequence", now U.S. Pat. No. 10,133,914, issued Nov. 20, 2018, which is a continuation of U.S. patent application Ser. No. 14/990,389, filed Jan. 7, 2016 to Hanina et al., now U.S. Pat. No. 9,652,665, issued May 16, 2017, titled "Identification and De-Identification Within a Video Sequence", which is a continuation of U.S. patent application Ser. No. 13/674,209, filed Nov. 12, 2012 to Hanina et al., now U.S. Pat. No. 9,256,776, issued Feb. 9, 2016, titled "Method and Apparatus for Identification", which, in turn, claims the benefit of U.S. Provisional Patent Application Ser. No. 61/582,969, filed Jan. 4, 2012 to Hanina et al., titled "Method and Apparatus for Identification." The contents of all of the prior applications are incorporated herein by reference in their entirety.

This application incorporates by reference the entire contents of the following applications, and any applications to which they claim priority, or otherwise incorporate by reference:

Method and Apparatus for Verification of Medication Administration Adherence, Ser. No. 12/620,686, filed Nov. 18, 2009 to Hanina et al.

Method and Apparatus for Verification of Clinical Trial Adherence, Ser. No. 12/646,383, filed Dec. 23, 2009 to Hanina et al.

Method and Apparatus for Management of Clinical Trials, Ser. No. 12/646,603, filed Dec. 23, 2009 to Hanina et al.

Apparatus and Method for Collection of Protocol Adherence Data, Ser. No. 12/728,721, filed Mar. 22, 2010 to Hanina et al.

Apparatus and Method for Recognition of Patient Activities when Obtaining Protocol Adherence Data, Ser. No. 12/815,037, filed Jun. 14, 2010, which claims the benefit of Apparatus and Method for Recognition of Patient Activities When Obtaining Protocol Adherence Data, U.S. Provisional Patent Application 61/331,872, filed May 6, 2010 to Hanina et al.

Apparatus and Method for Assisting Monitoring of Medication Adherence, Ser. No. 12/899,510, filed Oct. 6, 2010 to Hanina et al.

Apparatus and Method for Object Confirmation and Tracking, Ser. No. 12/898,338, filed Oct. 5, 2010 to Hanina et al.

Method and Apparatus for Monitoring Medication Adherence, Ser. No. 13/189,518, filed Jul. 12, 2011 to Hanina et al., which claims the benefit of Method and Apparatus for Monitoring Medication Adherence, 61/495,415, filed Jun. 10, 2011 to Hanina et al.

FIELD

This invention relates generally to the monitoring of patient medication adherence to a prescribed regimen, patient behavior, medical procedure or other patient or healthcare provider activity, and more particularly to obscuring the identity of a video recording of a patient, while allowing for adherence to a medication protocol, or adherence to other desired patient activity to be confirmed.

BACKGROUND

Determination of adherence of patients to a medication protocol is difficult. While direct observation may be employed, it may be expensive and inconvenient. Watching medication administration over a video conference may be employed, but is also expensive and inconvenient in that both the patent and an administrator must be on a video or other conference call at the same time. Finally, the inventors of the present invention have determined that these conventional systems fail to protect the identification and privacy of patients and patient data, while still allowing for determination patient activity.

SUMMARY

Therefore, in accordance with one or more embodiments of the invention, video sequences of patients administering medication may be recorded. The video sequences may be preferably de-identified in a manner to obscure patient identifying information while still allowing for a reviewer (either computerized or human) to determine proper medication administration from the video sequence. Additional embodiments of the invention may apply to activities performed by a healthcare provider, or other assistant, thus allowing for confirmation of proper action by them, while maintaining the privacy of the patient identification.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

Figure 1:
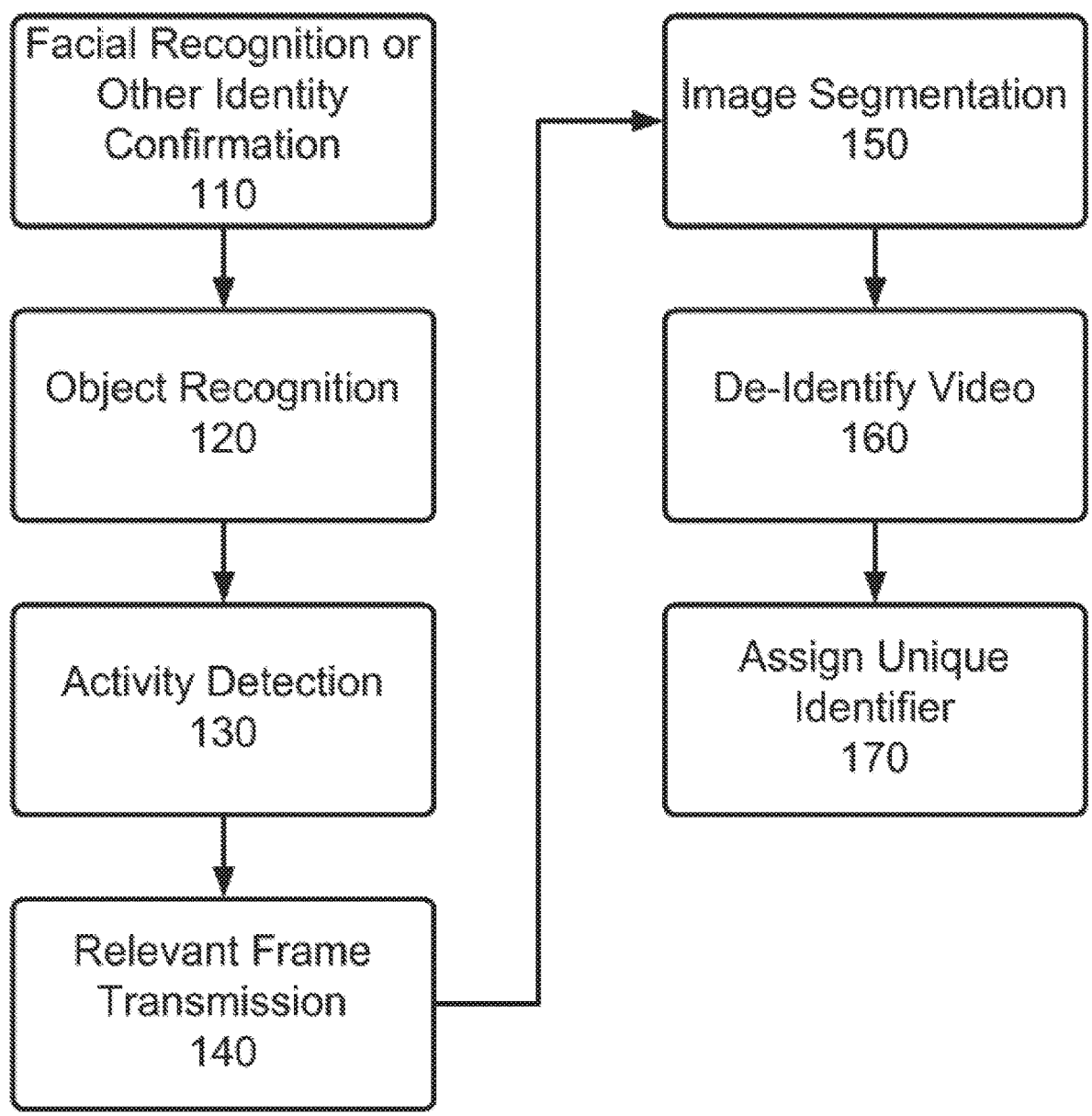
FIG. 1 is a flowchart diagram in which video frames are de-identified after transmission to a remote location in accordance with an embodiment of the invention.

Storing a video sequence of a patient or other individual taking medication to be later used to determine adherence to a particular medication protocol may comprise a difficulty as storage of such patient related information may run afoul of HIPAA or other patient privacy laws.

Therefore, in accordance with one or more embodiments of the invention, one or more methods or apparatuses depicted in one or more of the above applications incorporated herein by reference may be employed in order to record one or more video medication administration sequences by a user. These sequences are preferably de-identified before, upon or after storage, or before, upon or after transmission. The method of de-identification in a first embodiment of the invention includes blurring of various facial features of the patient so that the patient identity cannot be determined from the de-identified video sequences, but maintains an unblurred portion of the patient where the medication is to be administered Other de-identification methods may be employed, such as rotoscoping, substitution of an avatar or other cartoon-like character, or the like. If may also be desirable to overlay actual portions of a video sequence, such as an inhaler, blood pressure cuff, injectable medication administration device, and the like. It is contemplated in accordance with one or more embodiments of the invention that maintaining or providing such an unblurred portion of the image only be provided for one or a few number of frames determined to be at a critical time for determining patient medication adherence. Furthermore, an indicator, such as a border, highlight or the like may be provided to emphasize these unblurred portions. Other portions of the image may be blurred that are not in the region of interest, i.e. background or other areas of the image not necessary to determine proper medication administration.

In the case of taking a pill orally, in order to better protect the identity of a patient, it may be preferable to only unblurr the pill in the mouth region of the image, rather than the entire mouth region of the user. Alternatively, it is possible that the patient's mouth and surrounding area is preferably not blurred, thus providing a wider viewing area of the image. Furthermore, as noted above, it is possible to implement this unblurring process in only key frames for determining medication administration, or on all frames as desired. Such unblurring may be implemented when, for example, an object of interest is recognized in a frame, such as when it has been determined that a pill is correctly positioned on the screen, or the pill has been determined to have been placed in the mouth of the user. Such de-identification may also employ facial averaging, or any other technique that may be employed to remove patient identifiable information while still allowing for a determination of proper medication administration. Any of de-identification techniques noted in any of the above applications incorporated herein by reference may also be employed. The patient may be shown a de-identified version of their video images on a display of an image acquisition device, thus confirming to them that their privacy is being protected. Furthermore, the process may be applied to other procedures, such as surgery in a hospital, other hospital of healthcare provider scenarios, in medical education, or the like.

Furthermore, one or more preliminary steps, such as identification of a medication pill or the like, may not be blurred, as long as doing so will not compromise the identity of the patient, such as if the pill is in front of the face of the patient. In this case, other views of the pill may be unblurred, thus allowing for identification while preserving the secrecy of the identity of the patient.

The blurred video sequences may further be employed in an automated activity recognition sequence employing computer vision to determine whether the patient has properly administered the medication, or can be reviewed manually by a user to determine adherence to the protocol. A combination of these two methods may also be employed.

Referring first to FIG. 1, a method for employing the present invention in which video frames are de-identified after transmission to a remote location is depicted. As is shown in FIG. 1, at step 110, facial recognition or other identity confirmation may be employed. The identity of the patient may be confirmed through machine vision. Such facial recognition may be provided for differentiation between multiple users, or to simply confirm that a single person is the correct person. Additionally, such facial recognition may be employed to identify users sequentially, such as in the case of identifying a healthcare provider and then a patient. The face, hands, fingers, other body parts, or gestures being made by a particular body part of the patient may be tracked through the screen to allow for continuous identification of position determination, if desired. Alternatively, one or more biometric markers, password or other acceptable identification techniques may be employed. Then at step 120, object detection may be employed to confirm proper medication is being employed. Next, at step 130 activity recognition may be employed in order to determine whether the patient has performed a particular desired step or steps, preferably related to medication administration or ingestion. Machine learning and computer vision may be employed in this step. This activity recognition step may be performed before step 120, in parallel with step 130, or after step 130.

Next, a number of relevant video frames may be selected for transmission at step 140. Thus, frames comprising a number of frames comprising those needed for object and activity recognition may be selected for transmission, including a predetermined number of leading and following frames. Such selection may be employed to reduce the amount of data to be transmitted and possibly reviewed. Of course, the entire recorded video sequence may also be transmitted. Such selection may be performed in an automated manner, such as a predetermined number of frames before and after some critical object, activity recognition, recognition of suspicious behavior, predetermined frames in relation to one or more instruction prompts, UI guides, or the like. In such a case, selection of video frames to be reviewed may be performed upon receipt of transmitted frames at the remote location, or all of the frames may be stored at the remote location. It should also be understood that such transmission is intended to include transmission to a remote storage device, such as a remote computer network, database, cloud storage or the like, and may also comprise transmission to a storage device on a local area network, via the Internet, or to a locally attached storage device. Such transmission may also take place from a mobile device to any of the remote locations described above, and may comprise any appropriate apparatus for acquiring and processing data, and then transmitting the processed data.

Once received after transmission, image segmentation may be performed at step 150 to segment the background and other portions of the image from the patient and medication, and may be employed to desegment the mouth and medication area from the rest of the image, if desired. This segmentation step may be skipped, if desired, or may only be applied to a subset of the transmitted images. Thus, such segmentation processing may only be applied to particular frames based upon proximity to item or gesture recognition, or in some other manner as noted above. The segmented patient images (or unsegmented images) may then be subject to de-identification processing at step 160, as described above, to remove the ability to identify the patient from the images, while retaining the ability to view the video sequence and confirm proper medication administration. Portions of one or more of the images may not be de-identified in a manner in accordance with the process as described above. Patient faces may be tracked through the various video image sequences to continue to confirm identity, to link face with other biometric identity confirmation to be sure the patient does not leave the screen, and may be used to confirm proximity of the patient to the screen, if desired, to allow for proper viewing of administration at a later time, by either automated or manual review. As an alternative in all embodiments, tracking or object recognition of the mouth portion and medication pill portion of the image may be employed, allowing or the blurring of the remainder of the image determined to be other than the tracked mouth and/or medication pill, and such partial blurring may be applied only in selected frames, as described above.

After such de-identification, a unique user identifier may be assigned to the de-identified video sequence at step 170 so that any user may view the video information without learning the identification of the patient, thus preferably complying with one or more desired privacy schemes. This identifier may be related to a particular patient, particular image capture device, or the like. The patient will therefore be un-identifiable from the de-identified video image sequence, but the sequence will be attributable and pinned to a particular patient record, thus allowing for proper correlation by one or more healthcare providers able to access such identification information.

Figure 2:
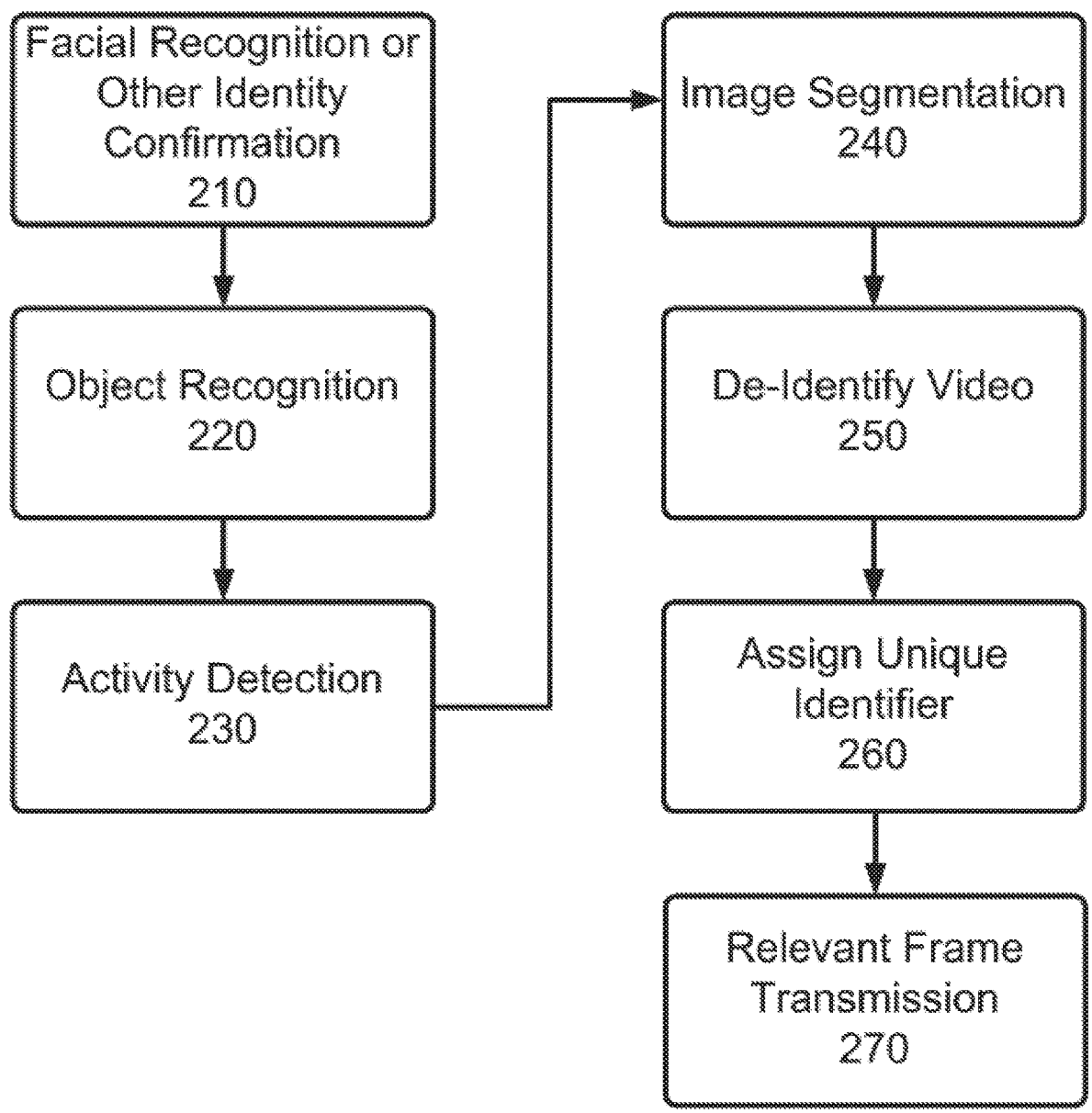
FIG. 2 is a flowchart diagram including object and activity recognition in which video frames are de-identified before transmission to a remote location in accordance with an additional embodiment of the invention.

Referring next to FIG. 2, a method for employing the present invention in which video frames are de-identified before transmission to a remote location is depicted. As is shown in FIG. 2, at step 210, facial recognition or other identity confirmation may be employed. The identity of the patient may be confirmed through machine vision. Alternatively, one or more biometric markers, password or other acceptable identification techniques may be employed. Then at step 220, object detection may be employed to confirm proper medication is being employed. Next, at step 230 activity recognition may be employed in order to determine whether the patient has performed a particular desired step or steps, preferably related to medication administration or ingestion. Machine learning and computer vision may be employed in this step, in any known manner, such as those set forth in one or more of the above applications incorporated herein by reference. This activity recognition step may be performed before step 220, in parallel with step 230, or after step 130.

Image segmentation may next be performed at step 240 to segment the background and other portions of the image from the patient and medication, and may be employed to desegment the mouth and medication area from the rest of the image, if desired. This segmentation step may be skipped, if desired, or may only be applied to a subset of the transmitted images. Thus, such segmentation processing may only be applied to particular frames based upon proximity to item or gesture recognition, or in some other manner as noted above. Facial or other identification processing may be employed at this time to confirm the identity of the user.

Other identification methods may also be used, either alone or in combination, including, but not limited to, fingerprint recognition, voice recognition, or password. After determining such identity, the segmented (or unsegmented) patient images may then be subject to de-identification processing at step 250, as described above, to remove the ability to identify the patient from the images, while retaining the ability to view the video sequence and confirm proper medication administration and ingestion. Portions of one or more images may not be de-identified in a manner in accordance with the process as described above. As an alternative in all embodiments, tracking or object recognition of the mouth portion and medication pill portion of the image may be employed, allowing or the blurring of the remainder of the image determined to be other than the tracked mouth and/or medication pill. Such partial blurring may also be only applied in one or more selected frames, in accordance with the process noted above. Tracking of other body portions may be employed for any particular desired test, such as tracking the arm of a user to be sure a blood pressure cuff is properly used, or to determine whether other testing (such a drug or urine testing) has been properly performed.

After such de-identification, a unique user identifier may be assigned to the de-identified video sequence at step 260 so that any user may view the video information without learning the identification of the patient, thus preferably complying with one or more desired privacy schemes. This identifier may be related to a particular patient, particular image capture device, or the like.

Next, a number of relevant video frames may be selected for transmission at step 270. Thus, frames comprising a number of frames comprising those needed for object and activity recognition may be selected for transmission, including a predetermined number of leading and following frames. Such selection may be employed to reduce the amount of data to be transmitted and possibly reviewed. Of course, the entire recorded video sequence may also be transmitted. Such selection may be performed in an automated manner, such as a predetermined number of frames before and after some critical object, activity recognition, recognition of suspicious behavior, predetermined frames in relation to one or more instruction prompts, UI guides, or the like. In such a case, selection of video frames to be reviewed may be performed upon receipt of transmitted frames at the remote location, or all of the frames may be stored at the remote location. It should also be understood that such transmission is intended to include transmission to a remote storage device, such as a remote computer network, database, cloud storage or the like, and may also comprise transmission to a storage device on a local area network, via the Internet, or to a locally attached storage device. Such transmission may also take place from a mobile device to any of the remote locations described above, and may comprise any appropriate apparatus for acquiring and processing data, and then transmitting the processed data. This frame selection step 270 may also be performed before the image segmentation and de-identification steps 250 and 260 if desired in order to reduce computational power requirements.

Figure 3:
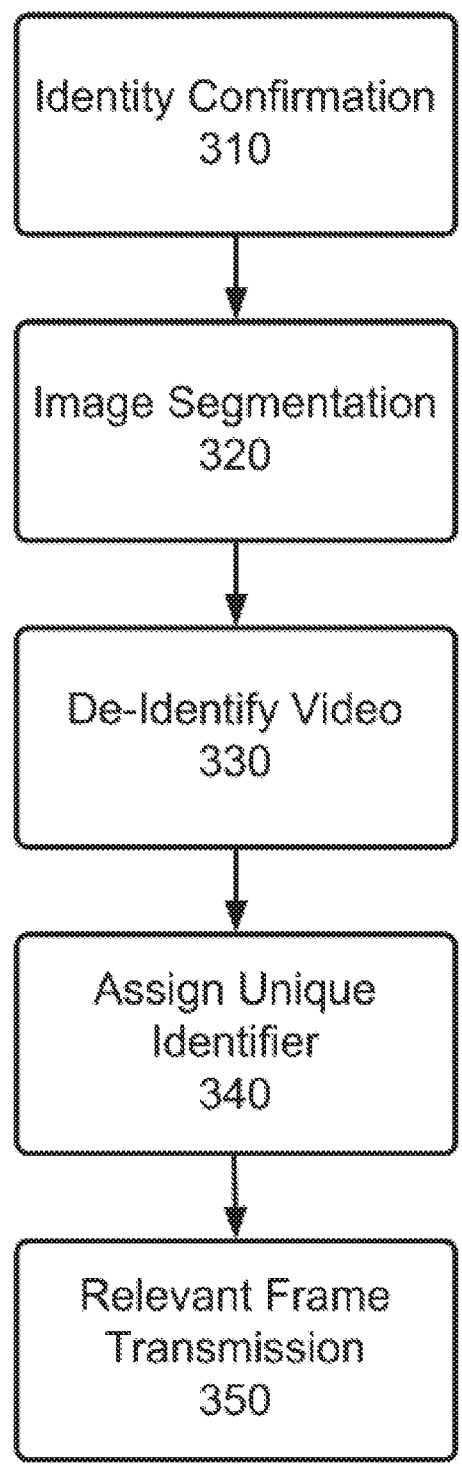
FIG. 3 is a flowchart diagram in which video frames are de-identified before transmission to a remote location in accordance with an additional embodiment of the invention.

Referring next to FIG. 3, a method for employing the present invention in which video frames are de-identified before transmission to a remote location is depicted. As is shown in FIG. 3, at step 310, facial recognition or other identity confirmation may be employed. The identity of the patient may be confirmed through machine vision, or through other methods, such as analyzing the biometrics of a person, including face, fingerprint, palm print, voice and the like. Alternatively, one or more biometric markers, password or other acceptable identification techniques may be employed. Image segmentation may next be performed at step 320 to segment the background and other portions of the image from the patient and medication, and may be employed to desegment the mouth and medication area from the rest of the image, if desired. This segmentation step may be skipped, if desired, or may be applied to a subset of the transmitted images. Thus, such segmentation processing may only be applied to particular frames based upon proximity to a particular determination of item or gesture recognition, or in some other manner as noted above. The segmented (or unsegmented) patient images may then be subject to de-identification processing at step 330, as described above, to remove the ability to identify the patient from the images, while retaining the ability to view the video sequence and confirm proper medication administration and/or ingestion, inhalation, injection or the like as appropriate. Portions of one or more of the images may not be de-identified in a manner in accordance with the process as described above. As an alternative in all embodiments, tracking or object recognition of the mouth portion and medication pill portion of the image may be employed, allowing or the blurring of the remainder of the image determined to be other than the tracked mouth and/or medication pill. And such partial blurring may be applied in only selected frames, as described above. After such de-identification, a unique user identifier may be assigned to the de-identified video sequence at step 340 so that any user may view the video information without learning the identification of the patient, thus preferably complying with one or more desired privacy schemes. This identifier may be related to a particular patient, particular image capture device, or the like. The patient will therefore be unidentifiable from the de-identified video image sequence, yet the sequence will be attributable and pinned to a particular patient.

Next, a number of relevant video frames may be selected for transmission at step 350, or alternatively, this step may be performed before image segmentation and de-identification steps 320 and 330, if desired, in order to reduce computational power requirements. Thus, frames comprising a number of frames comprising those needed for object and activity recognition may be selected for transmission, including a predetermined number of leading and following frames. Such selection may be employed to reduce the amount of data to be transmitted and possibly reviewed. Of course, the entire recorded video sequence may also be transmitted. Such selection may be performed in an automated manner, such as a predetermined number of frames before and after some critical object, activity recognition, recognition of suspicious behavior, predetermined frames in relation to one or more instruction prompts, UI guides, or the like. In such a case, selection of video frames to be reviewed may be performed upon receipt of transmitted frames at the remote location, or all of the frames may be stored at the remote location. It should also be understood that such transmission is intended to include transmission to a remote storage device, such as a remote computer network, database, cloud storage or the like, and may also comprise transmission to a storage device on a local area network, via the Internet, or to a locally attached storage device. Such transmission may also take place from a mobile device to any of the remote locations described above, and may comprise any appropriate apparatus for acquiring and processing data, and then transmitting the processed data.

Figure 4:
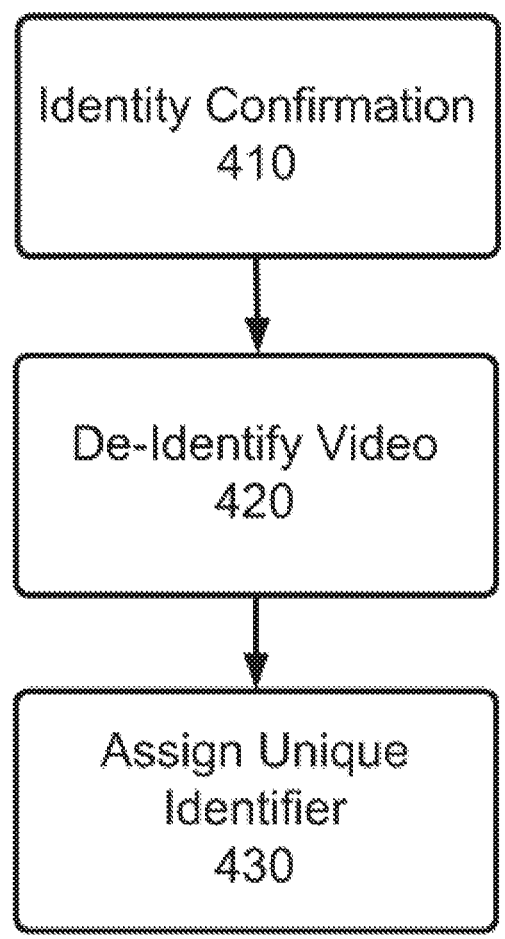
FIG. 4 is a flowchart diagram in which video frames are de-identified before and assigned a unique identifier in accordance with an additional embodiment of the invention.

Referring next to FIG. 4, a method for employing the present invention in which video frames are de-identified before transmission to a remote location is depicted. As is shown in FIG. 4, at step 410, identity confirmation may be employed. The identity of the patient may be confirmed through machine vision, facial recognition or the like. Alternatively, one or more biometric markers, password or other acceptable identification techniques may be employed. Acquired patient images may then be subject to de-identification processing at step 420, as described above, to remove the ability to identify the patient from the images, while retaining the ability to view the video sequence and confirm proper medication administration. Portions of one or more of the images may not be de-identified in a manner in accordance with the process as described above. Such partial blurring may be applied only in selected frames, as described above.

After such de-identification, a unique user identifier may be assigned to the de-identified video sequence at step 430 so that any user may view the video information without learning the identification of the patient, thus preferably complying with one or more desired privacy schemes. This identifier may be related to a particular patient, particular image capture device, or the like. A unique identifier may also be provided for the medication being administered by the patient, if desired. Such a medication may be identified using gesture recognition, object detection or the like.

Each of the above-described embodiments of the invention allows rapid review and streaming of a video sequence acquired of a patient administering medication from a server along with time, date, location, unique identifier, dose taken, medication name, and other patient activities that have been automatically logged, while maintaining the privacy of the patent identity and any other confidential or private patient information. Such rapid review may include the automated (or manual) designation of a portion of the total sequence of images that may or may not include a non-de-identified portion for review by a viewer. Thus, a predetermined number of frames before and after an event, such as before and after object detection of a medication, or gesture or activity recognition of ingestion or other medication administration, may be designated. As such, only these designated frames need be shown to the user, thus resulting in a substantially reduced set of images for review by a viewer. This may allow for a rapid review of a large number of medication administration sequences by the viewer. If the full video sequence is desired to be provided, it is contemplated in accordance with an alternative embodiment of the invention that the viewer be provided with the ability to skip or "fast forward" the video sequence to each of one or more groups of designated "important" frames, preferably displaying non-de-identified video portions, and preferably being designated as noted above in accordance with object, activity or other recognition. A slider or other time or location selection device may also be provided to allow a viewer to quickly and easily review and select various portions of a video sequence. Annotation of the video sequence may also be provided to allow for notes to be saved for further review, for example.

In order to further aid the viewer, it is contemplated in accordance with one or more various embodiments of the invention that one or more portions of one or more of the non-de-identified frames, or of the de-identified frames, be highlighted, zoomed, or otherwise amplified or highlighted in order to allow for a more precise review thereof by a viewer. This will allow the viewer to better determine suspicious behavior, proper administration and ingestion, or the like. Such highlighting may be performed in an automated manner based upon such recognition, or may be provided in a manual manner, such as indicating an item to be highlighted by an operator. Once highlighted, the highlighted area may be tracked through a sequence of frames so that the object, such as a medication, can be followed through a video sequence.

Various embodiments of the present invention may further employ face tracking that would track the user, eliminate other faces or other distracting or possibly identifying items in the video sequences. Such tracking may be employed in real-time, near-real time, or after storage and or transmission of the video sequence data. Upon use of such face tracking, it is contemplated in accordance with embodiments of the invention that if the face of the patient leaves the screen, the entire screen may be blurred, or otherwise de-identified. Furthermore, if the face of the patient turns sideways or to another difficult to see angle, the entire screen may be blurred. Whether the face or other object, even if completely blurred, tracking technologies may still be employed to confirm location of the patient face, object, or the like.

Such processing may be applicable to medication administration, and any other patient procedures, including in hospital, doctor office, outpatient, home or other settings. Thus, in accordance with various embodiments of the invention, administration of any item may be determined, while maintaining privacy of the user, by blurring or otherwise de-identifying video image sequences, while maintaining non-blurred video portions including the administration procedure.

Figure 5:
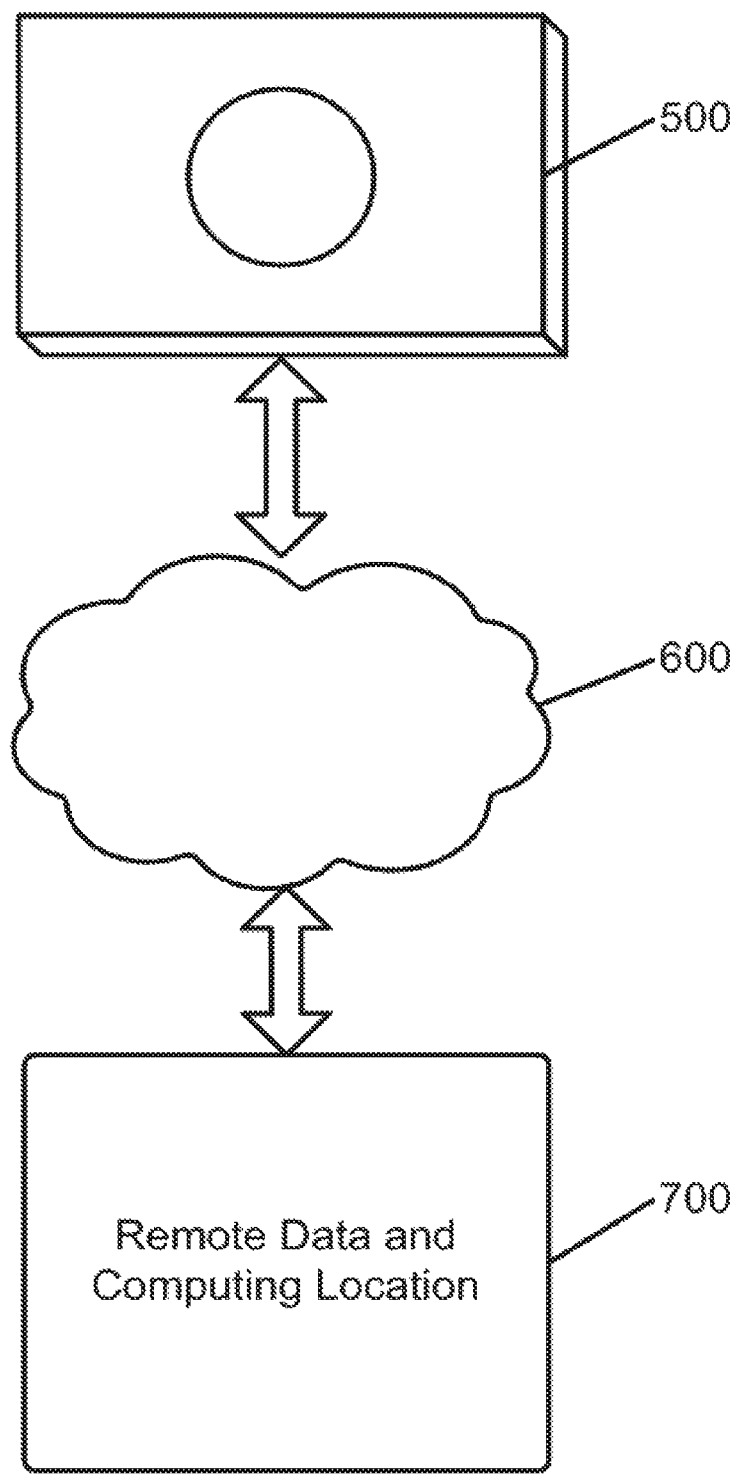
FIG. 5 depicts a data transmission relationship between a video capture device and a remote storage and computing location in accordance with an embodiment of the invention.

In accordance with various embodiments of the invention, referring next to FIG. 5, a remote information capture apparatus 500 is shown. Such apparatus is adapted to allow for the capture and processing of information in order to implement the system and method in accordance with the applications noted above and incorporated herein by reference. Such information capture apparatus 500 is placed in communication with a remote data and computing location 700 via a communication system 600, preferably the Internet or other communication system, such as wireless communication, wireless LAN, or any other communication system appropriate for transmitting video and other data. Via communication system 600, information captured by apparatus 500 is transmitted to remote data and computing location 700, and analysis information or other instructions may be provided from remote data and computing location 700 to apparatus 500. In accordance with a preferred embodiment of the invention, any data to be transmitted may first be encrypted on apparatus 500 and unencrypted at remote data and computing location 700. Indeed, it is contemplated in accordance with one or more of the noted embodiments of the invention that encryption of recorded information, either before or after de-identification thereof, will improve security of patient identification and robustness of the system in general.

It is further contemplated that a plurality such information capture apparatuses 500 may be coordinated to monitor a larger space than a space that can be covered by a single such apparatus. Thus, the apparatuses can be made aware of the presence of the other apparatuses, and may operate by transmitting all information to one of the apparatuses 500, or these apparatuses may each independently communicate with remote data and computing location, which is adapted to piece together the various information received from the plurality of devices 500. Each such apparatus 500 may comprise a mobile computing device, such as a smart phone or the like including a web camera, or a laptop computer or pad computing device, each including a web camera or the like. Therefore, in accordance with one or more embodiments of the invention, Processing of video information may be performed locally, remotely, or partially locally and remotely. Thus, de-identification and object and/or activity recognition may proceed locally, while frame selection may proceed remotely. Any other combination of locally and remote processing may also be provided, also including encryption and decryption schemes. Furthermore, and local remote, or combination of devices may each process a portion of the captured information, and may then transmit processed information to a single location for assembly. Finally, encryption of video may be performed locally, and then after decryption, all processing described above may be performed. Such remote location may comprise a cloud location, remote computer or group of computers, a remote processor or multiple processors, and the like, and may further include one or more attached or further remote storage devices for storing computer, computer program and/or video information.

Figure 6:
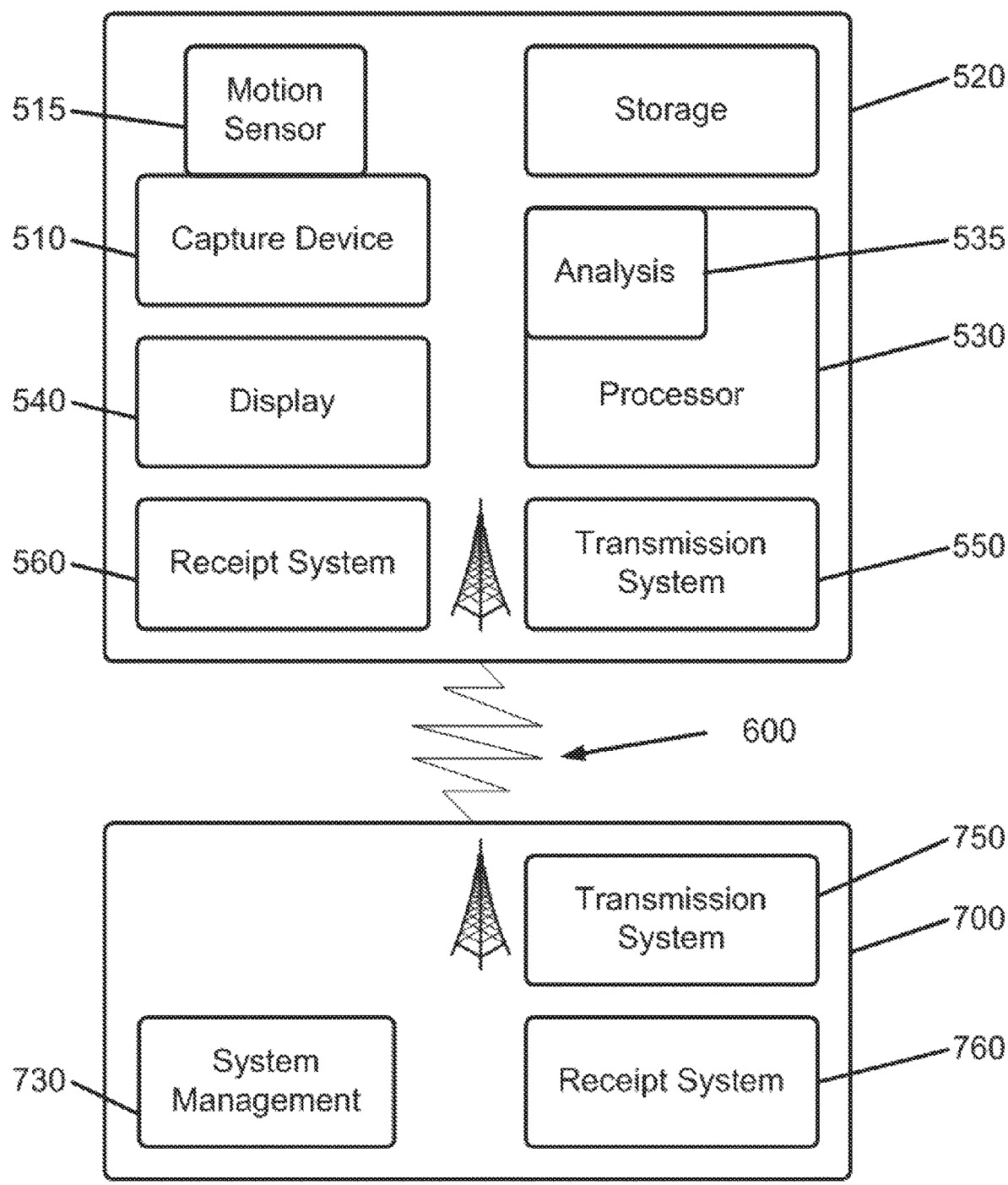
FIG. 6 depicts details of both the video capture device and remote storage and computing location of FIG. 5.

Referring next to FIG. 6, a more detailed view of a preferred embodiment of remote information capture apparatus 500 and remote data and computing location 700 is depicted. As is shown in FIG. 6, apparatus 500 comprises an information capture device 510 for capturing video and audio data as desired. A motion detector 515 or other appropriate trigger device may be provided associated with capture device 510 to allow for the initiation and completion of data capture. Information capture device 510 may comprise a visual data capture device, or may be provided with an infrared, night vision, or other appropriate information capture device. A storage location 520 may be further provided for storing captured information, and a processor 530 is provided to control such capture and storage, as well as other functions associated with the operation of remote information capture apparatus 500. An analysis module 535 is provided in accordance with processor 530 to perform a portion of analysis of any captured information at the remote information capture apparatus 500, in the manner as described above. Apparatus 500 is further provided with a display 540, and a data transmission and receipt system 550 and 560 for displaying information, and for communicating with remote data and computing location 700. Remote data and computing location 700 preferably comprises system management functions 730, and a transmission and reception system 750 and 760 for communicating with apparatus 500. Such system management functions comprise, at least in part, many of the centralized functions noted in any of the pending patent applications noted above and previously incorporated herein by reference, or any of the above described functions. Transmission and reception system 750 and 760 may further comprise various GPS modules so that a location of the device can be determined at any time, and may further allow for a message to be sent to one or more individual apparatuses, broadcast to all apparatuses meeting one or more determined requirements, or being used for administration of a particular prescription regimen, or broadcast to all available apparatuses. Remote location also may include computer processors, storage, etc. appropriate for performing all functions described above being performed at such a remote location, after transmission of video and other data from a local computing device.

It has been further determined by the inventors of the present invention that when employing object and activity detection to determine, for example, the identity of a medication, and more particularly when the medication pill has been placed in the mouth of a user, it may be difficult to determine the location of the medication pill, and thus confirm proper medication ingestion. This is because, in the case of a light colored or white medication pill, for example, the teeth of the user may look similar to the pill. Therefore in accordance with an embodiment of the invention, after (or instead of) a pill candidate has been identified during a step determining medication ingestion, a next step of processing may be performed to confirm that a mouth color surrounds the pill candidate. Thus, if the pill candidate turns out to be the tooth of a user, to the right and left of the tooth candidate will be other teeth, viewed as similarly colored by the video camera. Thus, by confirming that to the right and left, top and bottom of a pill candidate is mouth colored, it is possible to determine that the pill candidate is a single entity, and is therefore in the mouth of the user. Thus, by using a recognition system for recognizing a pill candidate surrounded by a mouth of a user, rather than simply looking for a medication pill, robustness of the object and activity recognition can be enhanced. This process may also be applied to isolation of a tongue piercing, for example. If not possible to remove such a piercing, the user may be asked to remove the piercing before using the system.

Similarly, when a user is moving a pill while holding it in their hand, it is possible to use the combination of the pill and fingertips of the user to differentiate the medication pill from other background items that may appear similar to a pill. Thus, through the tracking of motion of the medication pill through an expected path of travel, and segmentation of not only the medication pill, but also the fingertip/pill/fingertip combination, improved object and activity recognition may be achieved. In such a manner, in accordance with an additional embodiment of the invention, first, one or more objects may be detected and presented as pill candidates. Then, from this set of pill candidates, further segmentation may be performed to confirm whether the pill candidate is held between two finger tips to confirm and differentiate that the pill candidate is in fact a medication pill and not some other object. Of course, the determination may simply look for a pill/fingertip combination from the outset.

Furthermore, because individuals may each hold a pill differently, in accordance with yet another embodiment of the invention, two or more detection methods may preferably be used. Thus, in this particular embodiment, for example, in a first frame one may search for an oblong medication pill being held horizontally between fingertips, and in a second frame for the oblong medication pill being held vertically between fingertips. Of course, and number of different objects may be searched for, and in this example, orientation of the medication pill at 45 or 135 degrees may also be employed. Furthermore, these multiple methods may be employed on each frame, depending on processor speed. Employing these methods on different frames provides a more real-time analysis with a slower processor, for example. Furthermore, with the use of a multi-core processor, the different methods may be processed in parallel on the different cores without sacrificing the real time effect.

Instructional feedback may be provided to the user to aid in proper positioning. This real time feedback makes the user aware that the tracking system is in operation, and may reduce the likelihood that the user will try to trick the system. By searching for these various different types of images in sequential or different frames, the likelihood of properly identifying the medication pill, regardless of how it is handled, is greatly increased. Of course, rather than simply looking for differently oriented images, one could, for example, look for color in one or more frames, shape in one or more frames, markings in one or more frames, and any other type of identifier in similar groups of one or more frames. Thus, any of these recognition systems may be employed, essentially in parallel. Furthermore, the use of such a plurality of methods of detection may allow for increased confirmation of a correct medication pill being identified. Additionally, once the medication pill has been identified, it is possible to select the one attribute generating the highest confidence score, and then use this one attribute to continue to track the medication pill through subsequent frames of the video images.

As one goal of the present invention is to confirm proper medication adherence and ingestion of medication, small movements, micro audio sounds suggesting swallowing, or the like, of the user may be employed in order to further confirm proper medication administration, reducing the likelihood of a user tricking the system. So, for example, identification of any swallowing motions in the neck or throat, gullet movement, jaw movement, or audio information related to swallowing, such as sounds related to the swallowing of water or the like, may be further employed in order to lend additional confirmation to the ingestion of a medication pill. Therefore, in accordance with one or more embodiments of the present invention, teaching the system to recognize such micro movements may be employed in a manner similar to the teaching of the system to recognize the medication pill. These movements may be correlated in time to properly determine sequence of administration, and may be compared to the first use by the user of the system in a controlled environment, such as a clinic. Additionally, all of the features of the invention noted above may be applied to such micro movements, including non-de-identifying these micro movements, when recognized, in all or a subset of the frames of captured video as described above. It may be desirable to de-identify any micro audio sounds, such as through sound synthesis, audio mix, sampling or the like to further protect the identity of the user.

Furthermore, magnification of these movements may be provided so that manual subsequent review of these portions of the video sequences may be easier. Additionally, during video capture, these portions of the user may be zoomed, to appear larger in the frame, and allowing for an easier automated and manual determination of such micro movements. The combination of automatic recognition and/or manual review of these micro movements may be used in conjunction with any of the methods for confirming medication administration and ingestion noted within this application in order to improve the confidence with which medication administration and ingestion may be confirmed.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description is intended to cover all of the generic and specific features of the invention herein described and all statements of the scope of the invention which, as a matter of language, might be said to fall there between.

What is claimed:

1. A method for de-identifying a video sequence of a body portion performing a sequence comprising a test sequence, comprising:

capturing the video sequence comprising a plurality of individual frames, the plurality of individual frames including images of the body portion performing the test sequence;

designating one or more frames of the plurality of individual frames as comprising the body portion performing the test sequence, wherein at least one frame of the plurality of individual frames is non-designated;

identifying a first portion of each of the one or more designated frames to remain visible, wherein the first portion comprises the body portion performing the test sequence;

de-identifying a second portion, distinct from the first portion, of each of the one or more designated frames, so that the first portion comprising the body portion performing the test sequence remains visible;

de-identifying the at least one non-designated frame; and analyzing the video sequence, including the first portion that remains visible in the one or more designated frames.

2. The method of claim 1, wherein de-identifying the second portion of each of the one or more designated frames or de-identifying the at least one non-designated frame comprises blurring.

3. The method of claim 1, further comprising highlighting visible portions of the plurality of individual frames comprising the body portion performing the test sequence.

4. The method of claim 1, wherein the test sequence comprises one or more desired testing protocols.

5. The method of claim 1, further comprising transmitting one or more of the plurality of individual frames comprising at least some de-identified portion to a remote storage and computing location.

6. The method of claim 1, further comprising performing activity recognition on the captured video sequence to recognize the test sequence within the plurality of individual frames, wherein performing activity recognition to recognize the test sequence comprises:
  determining, through object recognition, an identity of an object for a first plurality of individual frames of the plurality of individual frames of the video sequence; and
  determining, through object recognition, the identity of the object and surroundings of the object in a second plurality of individual frames of the plurality of individual frames of the video sequence.

7. The method of claim 1, wherein the test sequence comprises micro movements of one or more body parts.

8. The method of claim 1, further comprising performing activity recognition on the captured video sequence to recognize the test sequence within the plurality of individual frames, wherein performing activity recognition to recognize the test sequence comprises:
  defining a plurality of detection methods for recognizing the test sequence; and
  applying each of the plurality of detection methods to a respective subset of the plurality of individual frames of the captured video sequence.

9. The method of claim 8, wherein each detection method comprises searching for a body part positioned at a respective different orientation.

10. A method for de-identifying a first video sequence of one or more users performing a sequence comprising a test sequence, comprising:

capturing the first video sequence comprising a plurality of individual frames, the plurality of individual frames including images of the one or more users performing a first test sequence;

designating one or more frames of the plurality of individual frames as comprising the one or more users performing the first test sequence, wherein at least one frame of the plurality of individual frames is non-designated;

identifying a first portion of the one or more designated frames to remain visible, wherein the first portion comprises the one or more users performing the first test sequence;

de-identifying a second portion, distinct from the first portion, of each of the one or more designated frames, so that the first portion comprising the one or more users performing the first test sequence remains visible;

de-identifying the at least one non-designated frame; and analyzing the first video sequence, including analyzing the first portions that remain visible in the one or more designated frames.

11. The method of claim 10, wherein de-identifying the second portion of each of the one or more designated frames or de-identifying the at least one non-designated frame comprises blurring.

12. The method of claim 10, further comprising highlighting visible portions of the plurality of individual frames comprising the one or more users performing the first test sequence.

13. The method of claim 10, further comprising transmitting the de-identified second portions of the one or more designated frames and the at least one non-designated frame to a remote storage and computing location.

14. The method of claim 10, further comprising performing activity recognition on the captured first video sequence to recognize the test sequence, wherein performing activity recognition comprises:
  determining, through object recognition, an identity of a body part for a first plurality of frames of the plurality of individual frames of the captured first video sequence; and
  determining, through object recognition, the identity of the body part and surroundings of the body part in a second plurality of frames of the plurality of individual frames of the captured first video sequence.

15. The method of claim 10, further comprising capturing a second video sequence, the second video sequence comprising a second plurality of individual frames, the second plurality of individual frames of the second video sequence including images of the one or more users performing a second test sequence;
  performing activity recognition on the captured second video sequence to recognize one or more micro movements of one or more body parts of a first user of the one or more users performing the second test sequence;
  designating one or more frames of the second plurality of individual frames of the captured second video sequence as comprising the recognized one or more micro movements of the one or more body parts of the first user performing the second test sequence, wherein at least one frame of the second plurality of individual frames of the captured second video sequence is non-designated;
  identifying a first portion of the designated one or more frames of the second plurality of frames of the captured second video sequence to remain visible, wherein the first portion of the designated one or more frames of the second plurality of frames of the captured second video sequence comprises the recognized one or more micro movements of the one or more body parts of the first user performing the second test sequence; and de-identifying a second portion of the designated one or more frames of the second plurality of frames of the captured second video sequence and de-identifying the at least one non-designated frame of the second plurality of frames of the captured second video sequence so that the first portion of the designated one or more frames of the second plurality of frames of the captured second video sequence remains visible; and analyzing the captured second video sequence comprising the recognized one or more micro movements of the one or more body parts of the first user performing the second test sequence.

16. The method of claim 15, further comprising performing activity recognition on the captured second video sequence to recognize the second test sequence, wherein performing activity recognition on the captured second video sequence comprises:

defining a plurality of detection methods for recognizing the second test sequence; and applying each of the plurality of detection methods to a respective subset of the second plurality of individual frames of the captured second video sequence.

17. The method of claim 16, wherein each of the plurality of detection methods comprise searching for the one or more body parts positioned at a respective different orientation.

18. A system for de-identifying a video sequence of a user performing a test sequence, the system comprising:

a video capture device, a processor, and a non-transitory computer-readable storage medium storing instructions that, when executed by the processor, cause the processor to perform operations comprising:

causing the video capture device to capture the video sequence comprising a plurality of individual frames, the plurality of individual frames including images of the user performing the test sequence, determining, through object recognition, an identity of a body part of the user for a first plurality of frames of the plurality of individual frames of the captured video sequence, determining, through object recognition, an identity of an object and surroundings of the object in a second plurality of frames of the plurality of individual frames of the captured video sequence, designating one or more frames of the plurality of individual frames of the captured video sequence as comprising a recognized action of the test sequence, wherein at least one frame of the plurality of individual frames of the captured video sequence is non-designated, identifying a first portion of each of the one or more designated frames to remain visible, wherein the first portion comprises a recognized placement of the object relative to the body part, de-identifying a second portion of each of the one or more designated frames, so that the first portion of each of the one or more designated frames remains visible;

de-identifying the at least one non-designated frame; and analyzing the captured video sequence, including analyzing visible portions of the one or more designated frames.

19. The system of claim 18, wherein de-identifying the second portion of each of the one or more designated frames or de-identifying the at least one non-designated frame comprises blurring.

20. The system of claim 18, wherein the operations further comprise applying each of a plurality of detection methods for recognizing a placement of the test sequence to a respective subset of the plurality of individual frames of the captured video sequence.

* * * * *